(12) United States Patent
Kim et al.

(10) Patent No.: US 7,964,747 B2
(45) Date of Patent: Jun. 21, 2011

(54) POLY(SILSESQUIOXANE) SPHERICAL PARTICLE CONTAINING ULTRAVIOLET LIGHT-ABSORBING GROUP AND MANUFACTURING METHOD THEREOF

(75) Inventors: Young-Baek Kim, Daejeon (KR); Kyung-Sup Yoon, Daejeon (KR); Mi-Jin Kim, Chungcheongbuk-do (KR); Mi-Sun Leem, Daejeon (KR)

(73) Assignee: Saimdang Cosmetics, Co., Ltd., Yeongdong-gun (KR)

( * ) Notice: Subject to any disclaimer, the term of this patent is extended or adjusted under 35 U.S.C. 154(b) by 437 days.

(21) Appl. No.: 11/587,916

(22) PCT Filed: Aug. 24, 2004

(86) PCT No.: PCT/KR2004/002129
§ 371 (c)(1),
(2), (4) Date: Oct. 26, 2006

(87) PCT Pub. No.: WO2005/105028
PCT Pub. Date: Nov. 10, 2005

(65) Prior Publication Data
US 2007/0249854 A1 Oct. 25, 2007

(30) Foreign Application Priority Data
Apr. 30, 2004 (KR) .................. 10-2004-0030555

(51) Int. Cl.
*C07F 7/10* (2006.01)
(52) U.S. Cl. ......... 556/419; 424/59; 424/60; 424/70.13; 424/70.14
(58) Field of Classification Search .............. 424/59, 424/60, 63, 69, 70.13; 556/419
See application file for complete search history.

(56) References Cited

U.S. PATENT DOCUMENTS

| | | | |
|---|---|---|---|
| 5,330,747 A | 7/1994 | Krzysik | |
| 5,451,610 A | 9/1995 | Krzysik | |
| 5,460,804 A | 10/1995 | Krzysik | |
| 5,512,272 A | 4/1996 | Krzysik | |
| 5,904,918 A | 5/1999 | Sterphone et al. | |
| 6,080,880 A | 6/2000 | Richard et al. | |
| 2004/0120915 A1* | 6/2004 | Yang et al. | 424/70.13 |
| 2004/0202627 A1* | 10/2004 | Kuroda et al. | 424/63 |

FOREIGN PATENT DOCUMENTS

| | | | |
|---|---|---|---|
| CN | 1465653 | * | 1/2004 |
| EP | 1 213 006 | | 6/2002 |
| JP | 08-027273 | * | 1/1996 |

OTHER PUBLICATIONS

J. Naciri, J. Y. Fang, M. Moore, D. Shenoy, C. S. Dulcey, and R. Shashidhar, Photosensitive Triethoxysilane Derivatives for Alignment of Liquid Crystals, Chem. Mater. 2000, 12, 3288-3295. © 2000 American Chemical Society.*

* cited by examiner

*Primary Examiner* — Ling-Siu Choi
*Assistant Examiner* — Bijan Ahvazi
(74) *Attorney, Agent, or Firm* — Greer, Burns & Crain Ltd.

(57) ABSTRACT

The present invention relates to a polysilsesquioxane spherical particle containing a ultraviolet light (UV) absorbing group, and manufacturing method thereof, characterized in that a preferred embodiment of the present invention comprises (i) preparing a silsesquioxane precursor containing the UV-absorbing group; and (ii) reacting the silsesquioxane precursor prepared in the step (i) with aminoalkylalkoxy silane compound or its oligomer under a solvent by means of a catalyst or a catalyst and co-polymerization precursor to prepare a polysilsesquioxane spherical particle containing a UV-absorbing group. The present invention provides the polysilsesquioxane spherical particle having a good physical property and a good UV-absorbing efficiency as cosmetic additive, and a simple and economical method of manufacturing the spherical particle.

6 Claims, 1 Drawing Sheet

POLY(SILSESQUIOXANE) SPHERICAL PARTICLE CONTAINING ULTRAVIOLET LIGHT-ABSORBING GROUP AND MANUFACTURING METHOD THEREOF

TECHNICAL FIELD

The present invention relates to a polysilsesquioxane spherical particle containing an ultraviolet light (UV) absorbing group, and a manufacturing method thereof.

BACKGROUND ART

It has been revealed that ultraviolet negatively affects skin, such as causing a skin cancer and a burn when anyone is exposed to sunlight for a long time. The cosmetics containing a UV-absorbing or shielding agent have been used to prevent such skin damage. However, it is possible that when the UV-absorbing and/or shielding agent added to the cosmetics are used in a form of molecule, the agents themselves may be adsorbed into skin, causing side effects.

In order to solve the above problems, many studies have been carried out to enhance skin safety by grinding an UV-shielding agent into small particles and adding the particles into the cosmetics. That is to say, the ultraviolet shielding agent was used as a UV-protective cosmetics additive by adhering or binding physical UV-shielding materials, for example titanium oxide and zinc oxide, to silicone resin particles. However, the cosmetics obtained from the method has problems of deteriorating its inherent property as well as of using a large amount of the UV-shielding agent and causing a stress whitening effect since it has poorer lubricating and elongating properties than that obtained by using a polyorganosilsesquioxane particle mentioned later.

Accordingly, many attempts have been carried out to use organosilsesquioxane such as polymethylsilsesquioxane, which is an insoluble resin forming a compact 3D network structure of a molecular frame, having a good fluidity and showing a gloss, and used as makeup cosmetic materials due to the lubricating and elongating properties (see Japanese Patent Publication Nos. 54-72300 and 60-13813), as the UV-absorbing or shielding agent.

However, there are various problems in manufacturing a polysilsesquioxane particle. For example, Japanese Patent Publication No. 63-77940 discloses that the particle is manufactured by polycondensation reaction in the interface between two layers of organic solutions. But this method has disadvantages of being difficult to control a stirring speed and maintain the interface during the reaction, and having a slow reaction rate due to the significantly low possibility of contacting with alkali metals.

Also, Japanese Patent Publication Nos. 2000-169583 and 2004-33927 disclose a manufacturing method wherein an emulsion is prepared and then its interface is used instead of the interface of the organic solutions. But this method has disadvantages that a process itself for manufacturing the emulsion is very complex, and that it is difficult to maintain the emulsion within a constant particle size.

In addition, Japanese Patent Publication No. 10-363101 discloses a method of manufacturing particles by adding water/butanol solution to organosilanetriol or its condensates obtained by hydrolyzing organotrialkoxysilane, followed by adding the resultant mixture to an alkaline aqueous solution. But this method has problems of being difficult to obtain small-size particles and having an extended reaction time and a low productivity.

Further, Japanese Patent Publication No. 2001-192452 discloses a method of manufacturing polysilsesquioxane particles by using an acid as a catalyst in a first process, and an alkaline aqueous solution as a neutralizing agent and a polycondensation reaction catalyst in a second process by using organotrialkoxysilane. But this method has a problem of going through a complex cascade reaction.

Also, Japanese Patent Publication No. S08-27273 discloses an attempt for manufacturing polyphenylsilsesquioxane containing an aromatic substituent, for example a phenyl group, to be used as a UV-absorbing cosmetics additive. But this method is subject to a complex process for purchasing and using spherical polysilsesquioxane particle having a mean particle diameter of 0.1 to 30 μm, as well as reacting diketone compounds (for example, benzoylacetone, acetylacetone and so oil) with aminoalkylalkoxysilane or the like to manufacture a polysilsesquioxane particle. And it also has a disadvantage of inevitably increasing temperature for the reaction.

DISCLOSURE OF INVENTION

Accordingly, the present invention is designed to solve the problems of the prior art, for example (i) poor physical properties such as a lubricating and elongating properties as a cosmetics additive upon use of physical UV-shielding materials, and alternatively (ii) a complex method of manufacturing a polysilsesquioxane particle and a low productivity thereof. Accordingly it is an object of the present invention to provide a polysilsesquioxane particle containing a ultraviolet light (UV) absorbing group which has good physical properties as a cosmetics additive, and a simple and economical method of manufacturing the particle.

The present invention relates to a polysilsesquioxane particle containing a UV-absorbing group, and a manufacturing method thereof, and specifically the present invention provides a polysilsesquioxane spherical particle containing a UV-absorbing group obtained by (i) preparing a silsesquioxane precursor (A) containing the UV-absorbing group; and (ii) reacting the silsesquioxane precursor (A) prepared in the step (i) with a compound (B) or its oligomer (B') of a following Chemical Formula 1 under a solvent by means of a catalyst or a catalyst and co-polymerization precursor, and a manufacturing method thereof:

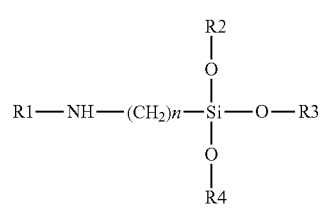

Chemical Formula 1 wherein R1 is selected from the group consisting of hydrogen, an alkyl group, an aminoketyl group, an aryl group, an aminoalkylaminoalkyl group, an aminoalkyl group, an aminocycloalkyl group, an aminoalkenyl group, an aminocycloalkenyl group and an aminoallyl group; n is an integral number of 1 to 3; R2, R3 and R4 are selected from the group consisting of an alkyl group, a cycloalkyl group, an alkenyl group, a cycloalkenyl group and an aryl group.

In the manufacturing method according to the present invention, the step (i) may comprise a step of reacting a chlorocarbonyl compound with an amino compound in the presence of a base to produce an amide compound, the chlorocarbonyl compound produced by substituting a hydroxy group of carboxylic acid with a halogen atom; using a carboxylic acid as an amino compound, and a coupling agent as a catalyst to produce an amide compound; or reacting a ester compound with an amino compound to produce an amide compound, the ester compound produced by reacting a carboxylic acid with a compound containing a hydroxy group under an acidic condition. And another general methods of manufacturing a trialkoxysilane compound containing the UV-absorbing group is also suitably applied in the present invention.

In the manufacturing method according to the present invention, the alkyl group, the cycloalkyl group, the alkenyl group, the cycloalkenyl group and the aryl group of the Chemical Formula 1 in the step (ii) may include, in particular, an alkyl group such as methyl, ethyl, propyl, butyl, pentyl, hexyl, heptyl, octyl, nonyl, decyl, undecyl, tridecyl, pentadecyl, heptadecyl and so on; an cycloalkyl group such as cyclopentyl, cyclohexyl and so on; alkenyl group such as vinyl, allyl, butenyl, pentenyl, hekicenyl, heptadecenyl and so on; cycloalkenyl group such as cyclohekicenyl and so on; aryl group such as phenyl, naphthyl and so on, and it is also possible to use compounds suitably substituted with the other group.

Preferably, the substituted compound includes 3-aminopropyltrimethoxysilane, 3-aminopropyltriethoxysilane, N-methyl-3-aminopropyltrimethoxysilane, N-methyl-3-aminopropyltriethoxysilane, N-(2-aminoethyl)-3-aminopropyltrimethoxysilane, N-(2-aminoethyl)-3-aminopropyltriethoxysilane, 4-aminobutyltrimethoxysilane, p-aminophenyltrimethoxysilane and so on. And 3-aminopropyltrimethoxysilane, N-(2-aminoethyl)-3-aminopropyltrimethoxysilane and so on are most preferred considering reactivity and easy handling.

Also in the step (ii) of the present invention, the alkaline solution may be used as a catalyst to reduce a reaction time, but said aminoalkyltrialkoxysilane and so on may preferably be used as a catalyst itself without the alkaline solution.

In addition, the step (ii) of the present invention provides a method of manufacturing a polysilsesquioxane spherical particle containing the UV-absorbing group in the presence of a solvent in a simple and easy manner, and also provides a method capable to manufacture the spherical particle in a easy manner in the absence of a thermostat.

Also, it is possible to control a suitable mean particle diameter of the spherical particle by adjusting a reaction solvent or reaction time and so on, or by suitably adjusting addition of small quantity of a surfactant. In addition, a spherical particle containing UV-absorbing groups in the inside and outside surfaces may be manufactured because a surface is not modified after a polysilsesquioxane particle is produced, but a compound containing a UV-absorbing group is directly used as a copolymerization precursor. It contributes to enhance UV-protecting efficiency of the polysilsesquioxane spherical particle containing the UV-absorbing group of the present invention.

The polysilsesquioxane particle according to the present invention may be manufactured under an alcoholic solvent such as methanol, ethanol, isopropanol, butanol and so on; an etheralcoholic solvent such as ethyleneglycolmethylether, ethyleneglycolethylether, propyleneglycolethylether and so on; an ether-based solvent such as tetrahydrofuran, dioxane and so on; a ketone-based solvent such as acetone, methylethylketone and so on; water; and a mixed solvent thereof, but it is most preferred to use water as the solvent in the step (ii) in terms of manufacturing cost and easy handling.

The reaction solvent of the first step may be manufactured under an alcoholic solvent such as methanol, ethanol, isopropanol, butanol and so on; an etheralcoholic solvent such as ethyleneglycolmethylether, ethyleneglycolethylether, propyleneglycolethylether and so on; an ether-based solvent such as tetrahydrofuran, dioxane and so on; a ketone-based solvent such as acetone, methylethylketone and so on; water; and a mixed solvent thereof, but it is most preferred to use water as the solvent in the step (ii) in terms of manufacturing cost, easy handling and safety of a product.

BRIEF DESCRIPTION OF THE DRAWINGS

These and other features, aspects, and advantages of preferred embodiments of the present invention will be more fully described in the following detailed description, taken accompanying drawing. In the drawing.

BEST MODES FOR CARRYING OUT THE INVENTION

Figure 1:
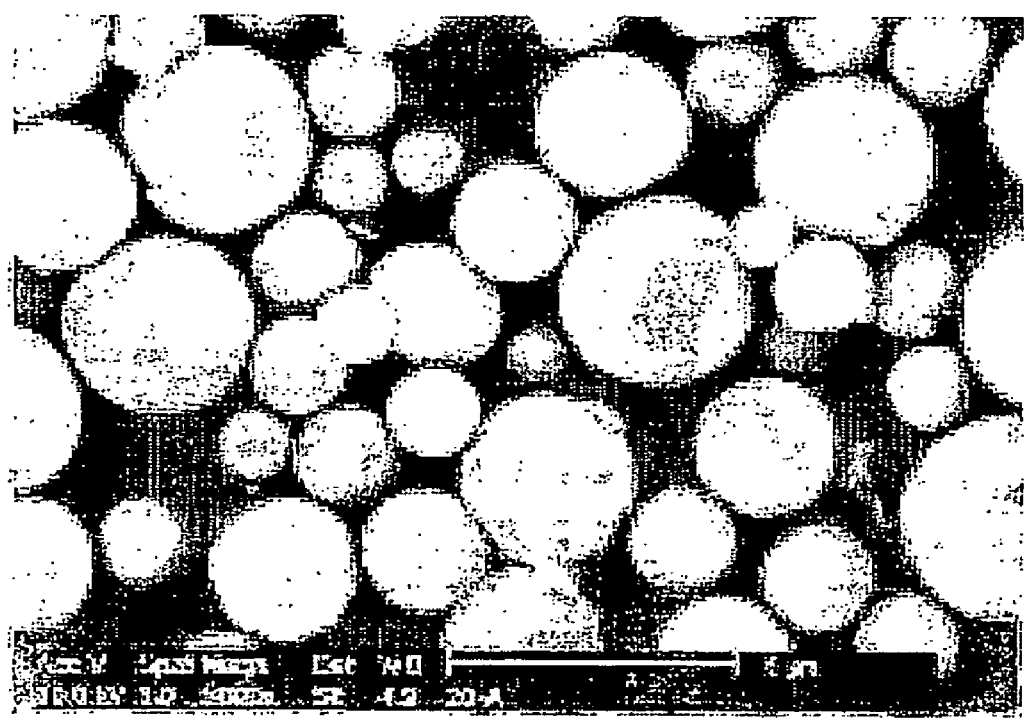
FIG. 1 is a scanning electron microscopic (SEM) picture showing polysilsesquioxane spherical particles according to the present invention.

Hereinafter, a polysilsesquioxane particle containing a UV-absorbing group, and a manufacturing method thereof according to the present invention will be described in detail with reference to the accompanying drawings.

A silsesquioxane precursor containing a ultraviolet light (UV) absorbing group of the step (i) according to the present invention is prepared according to methods described as follows. However in addition to the following the methods, the silsesquioxane precursor containing a UV-absorbing group may be prepared by means of suitable reactions by those skilled in the art pertaining to the present invention.

First in the step (i) of the manufacturing method according to the present invention, a chlorocarbonyl compound is produced by replacing with a halogen atom a hydroxy group of carboxylic acid containing a UV-absorbing group as shown in the following Reaction Formula 1. And the silsesquioxane precursor may be manufactured by reacting the chlorocarbonyl compound with aminoalkyltrialkoxysilane in the presence of a base.

Reaction Formula 1

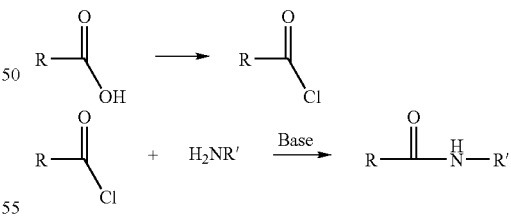

wherein R represents a UV-absorbing group, and R' represents alkyltrialkoxysilane.

As shown in the Reaction Formula 1, for example fluoro, bromo or iodide group may be used as a halogen atom instead of chloro group, and substituted organic amines such as diethylamine or triamine and so on may be also suitably used.

As an alternative, in the step (i) of the manufacturing method according to the present invention the silsesquioxane precursor may be manufactured using a method of manufacturing an amide compound by using a carboxylic acid containing the UV-absorbing group as an aminoalkyltrialkoxysilane compound, and a coupling agent as the catalyst, as shown in the following Reaction Formula 2.

Reaction Formula 2

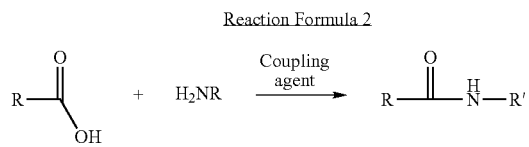

In the Reaction Formula 2, R represents a UV-absorbing group, and R' represents alkyltrialkoxysilane.

As the coupling agent, dicyclohexylcarbodiimide, diethylazocarboxylate or N,N'-carbonyldiimidazole may be used and it is most preferably suitable to use dicyclohexylcarboimide.

As another alternative, in the step (i) of the manufacturing method according to the present invention an ester compound containing the UV-absorbing group is manufactured by reacting carboxylic acid containing the UV-absorbing group with a material containing a hydroxy group under an acidic condition, as shown in the following Reaction Formula 3. And the silsesquioxane precursor may be manufactured using a method of manufacturing an amide compound by reacting the ester compound with aminoalkyltrialkoxysilane.

Reaction Formula 3

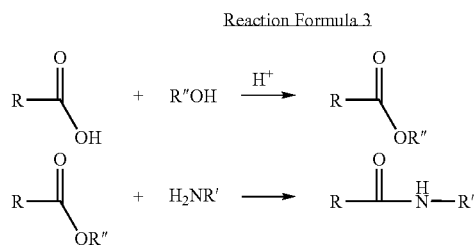

In the Reaction Formula 3, R represents a UV-absorbing group, R' represents alkyltrialkoxysilane, and R" represents alkyl containing 1 to 5 carbon atoms.

All of the methods of manufacturing the silsesquioxane precursor are available, but the method of manufacturing the compound of the Reaction Formula 2 is most preferably used in terms of a relatively low reaction temperature and easy removability of a resultant by-product.

If materials, for example cinnamic acid, methoxycinnamic acid, benzoic acid, N,N-dimethyl-p-aminobenzoic acid, N,N-dihydroxypropyl-p-aminobenzoic acid and so on, contain a group capable of absorbing the ultraviolet into its internal structure as the UV-absorbing group of the step (i) according to the present invention, the materials may be use as the silsesquioxane precursor containing the UV-absorbing group of the step (i) according to the present invention by suitably modifying the materials.

In the step (ii) of the present invention, the polysilsesquioxane spherical particle having a desired particle size and size distribution may be manufactured by adjusting the silsesquioxane precursor prepared in the step (i) and aminoalkylalkoxysilane used as the catalyst or the catalyst and co-polymerization precursor at an suitable administration ratio. Preferably, the particle size may be controlled by adjusting the silsesquioxane precursor and aminoalkylalkoxysilane at the administration ratio (% by weight) between 50:1 and 1:3. In this case, the resultant particle has a size in the range between several 10 nm and several 10 μm.

Also, it is possible to adjust the particle size and the size distribution by adding an adequate surfactant. Here the surfactant may be suitably used as sorbitan fatty acid ester such as sorbitan trioleate, sorbitansesquioleate, sorbitansesquistearate, sorbitanmonostearate, sorbitanmonolaurate, and sorbitanmonopalmitate; glycerin fatty acid ester such as glycerinmonostearate, and glycerinmonooleate; polyglycerin fatty acid ester such as diglycerindioleate, diglycerinmonooleate, diglycerinmonostearate, tetraglycerimnonooleate, and tetraglycerinmonostearate; pentaerythritol fatty acid ester such as pentaerythritolmonostearate, and pentaelythritolmonopalmitate; propyleneglycol fatty acid ester such as propyleneglycolmonostearate, and propyleneglycolmonolaurate; diethyleneglycol fatty acid ester such as diethyleneglycolmonostearate, and diethyleneglycolmonolaurate; polysaccharide fatty acid ester such as sucrosetristearate, sucrosepalmitate, and sucrosedilaurate; and cetyltriaminobromide and so on. Preferably, fatty acid ester such as polyoxyethylene sorbitan, for example Tween, and sorbitan fatty acid ester, for example Span are suitably used.

It is easy to adjust the particle size in a range between several 10 nm and several 10 μm by adjusting each amount of alkoxysilane including the amino group, surfactant and solvent (water), and reaction time, etc. In particular, It is easy to adjust diameter of the particle in a range between several 10 nm and several 10 μm by adding the surfactant at amount between 0.1 and 3.0% by weight.

In another preferred aspect of the step (ii) according to the present invention, the particles are spontaneously generated only when desired materials are mixed merely without intentionally varying a specific early or intermediate reaction condition. Also acceptable temperature in the manufacturing method of the present invention ranges from normal temperature to 100° C., and it is possible to increase the temperature under high pressure.

Hereinafter, the present invention will be fully described in the following preferred embodiments. However, the description proposed herein is just a preferable example for the purpose of illustrations only, not intended to limit the scope of the invention, so it should be understood that other equivalents and modifications could be made thereto without departing from the spirit and scope of the invention.

Example 1

(i) Preparation of a Silsesquioxane Precursor Containing a UV-Absorbing Group

N-trimethoxysilylpropyl-p-methoxycinnamamide was prepared, as shown by a following Chemical Formula 2.

Chemical Formula 2

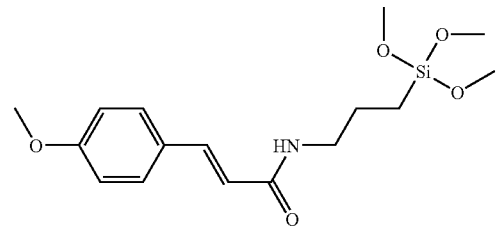

30 g of p-methoxycinnamic acid and 35.1 g of dicyclohexylcarbodiimide were added to a 1 L round 3-necked flask equipped with a dropping funnel and a cooler, 600 mL of toluene newly distilled from sodium ketyl was added thereto, and the resultant mixture was refluxed to yield a homogeneous solution. After about 30 minutes, 37.5 g of 3-aminopropyltrimethoxysilane was dropped over 30 minutes through the dropping funnel. The resultant reaction mixture was refluxed for 4 hours, and then toluene was removed by vacuum distillation without contacting with moisture. Dicyclohexyl urea formed in a remaining solution was removed by filtration to yield a product. The resultant product was determined using FT-IR and thin layer chromatography (TLC). Yield of the resultant product is about 40 g.

(ii) Preparation of a Polysilsesquioxane Spherical Particle

A polysilsesquioxane spherical particle was prepared by using N-trimethoxysilylpropyl-p-methoxycinnamamide prepared in the step (i) as a silsesquioxane precursor. 6 g of N-trimethoxysilylpropyl-p-methoxycinnamamide was dispersed in 3 L of distilled water, and 6 g of 3-aminopropyltrimethoxysilane was added thereto, and then the resultant mixture was stirred for 24 hours at normal temperature. Subsequently, a precipitate was harvested by centrifugation, washed with water once again to yield a polysilsesquioxane spherical particle containing a p-methoxycinnamamide group as a UV-absorbing group. Mean diameter of the resultant spherical particle was determined from an image of a scanning electron microscope (SEM; Philips, XL-30S). Diameters of 50 spherical particles shown in a scanning electron microscopic photograph were calculated to estimate their mean as a mean diameter. As a result, the mean diameter of the spherical particles was about 1.5 µm. The scanning electron microscopic photograph of the resultant silsesquioxane spherical particle is shown in FIG. 1.

Example 2

(i) Preparation of a Silsesquioxane Precursor Containing a UV-Absorbing Group

The silsesquioxane precursor containing the UV-absorbing group, or example trimethoxysilylpropylbenzamide was prepared, as shown by a following Chemical Formula 3.

Chemical Formula 3

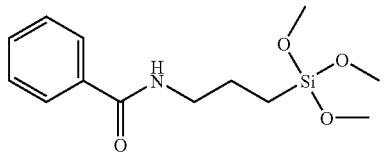

7.8 g of benzoyl chloride and 50 mL of toluene dried in sodium ketyl and distilled just before its use were added to a 250 mL 3-necked flask equipped with a dropping funnel, and a mixture of 10 g of 3-aminopropyltrimethoxysilane and 7.8 g of triethylamine was dropped over 20 minutes with stirring. About 18 hours after dropping was completed, the mixture was filtered, the precipitate was removed, and toluene was vacuum distilled out to yield a product. A purity of the resultant product was roughly determined using FT-IR (Bomem MB 104) and silica-coated thin layer chromatography. From a result of thin layer chromatography, it was confirmed that the resultant product mainly comprise one main product, and amide is formed around a 1,700 cm$^{-1}$ peak of IR.

(ii) Preparation of Polysilsesquioxane Spherical Particle

A polysilsesquioxane spherical particle was prepared by using trimethoxysilylpropylbenzamide prepared in the step (i) as a silsesquioxane precursor. 10 g of trimethoxysilylpropylbenzamide was dispersed in distilled water, 1 g of aminopropyltrimethoxysilane was added thereto, and the resultant mixture was slowly stirred for 24 hours at normal temperature to prevent the spherical particle from being coagulated. And then the reaction was completed. After 24 hours, it was confirmed that the particle was coagulated using a light microscope. And then the coagulated particle was centrifuged, and the precipitate was harvested and washed with water once again to yield a polysilsesquioxane spherical particle containing the benzamide group as the UV-absorbing group, the particle having diameter of about 2 µm. Size of the spherical particle was determined by averaging diameter of spheres observed in a scanning electron microscope (Philips, XL-30s). It was confirmed that a benzene group and Si—O—Si were formed using FT-IR.

Example 3

(i) Preparation of a Silsesquioxane Precursor Containing a UV-Absorbing Group

The silsesquioxane precursor containing the UV-absorbing group, for example trimethoxysilylpropylcinnamamide was prepared, as shown by a following Chemical Formula 4.

Chemical Formula 4

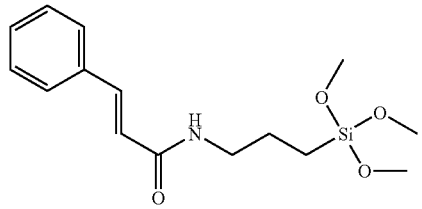

40 g of cinnamic acid and 50 g of dicyclohexylcarbodiimide were added to a 1 L round 3-necked flask equipped with a dropping funnel and a cooler, and also 600 mL of toluene newly distilled from sodium ketyl was added thereto, and the resultant mixture was refluxed to yield a homogeneous solution. After about 30 minutes, 48 g of 3-aminopropyltrimethoxysilane was dropped over 30 minutes through the dropping funnel. The resultant reaction mixture was refluxed for 4 hours, and then toluene was removed by vacuum distillation without contacting with moisture. Dicyclohexyl urea formed in a remaining solution was removed by filtration to yield a product. The resultant product was determined using FT-IR and thin layer chromatography. Yield of the resultant product is about 30 g.

(ii) Preparation of Polysilsesquioxane Spherical Particle

A polysilsesquioxane spherical particle was prepared by using trimethoxysilylpropylcinnamamide prepared in the step (i) as a silsesquioxane precursor. 6 g of trimethoxysilylpropylcinnamamide was dispersed in distilled water, and 6 g of N-(2-aminoethylamino)-3-aminopropyltrimethoxysilane was added thereto, and then the resultant mixture was stirred for 24 hours at normal temperature to yield a polysilsesquioxane spherical particle. The spherical particle was harvested by distillation, and dried at normal temperature until constant mass was maintained to yield 3.5 g of a spherical particle having a diameter of 2 μm. Diameter was calculated in the same apparatus and method as described in Example 1. The particle was observed using a modified method of Example 1.

Example 4

Test of Confirming Ultraviolet Absorption

An ultraviolet absorption was tested in a form of particle for the spherical particle obtained in Example 3 using an ultraviolet spectrophotometer Shimazu UV 2450. As a result, the spherical particle showed 100% of ultraviolet absorptance at 310 nm, starting to absorb ultraviolet from 325 nm.

Example 5

Effect of an Added Surfactant 30 g of N-trimethoxysilylpropyl-p-methoxycinnamamide prepared in the same the method as Example 1 was dispersed in 3 L of a 0.01% Tween 20 aqueous solution, 6 g of N-(2-aminoethyl)-3-aminopropyltrimethoxysilane was added thereto, and then stirred for 24 hours at normal temperature to prepare a spherical particle. The spherical particle was harvested by centrifugation, washed with a sufficient amount of ethanol, centrifuged once again, and then dried at normal temperature until constant mass was maintained to yield 15 g of a spherical particle. Mean diameter was calculated according to the method of Example 1. As a result, mean diameter of the particle was 600 nm.

Example 6

Measurement of a Solar Protection Factor of the Spherical Particle

A solar protection factor of the spherical particle prepared in Example 5 was evaluated under the condition of 25° C. and 60% relative humidity as follows (see Korea Food & Drug Administration Notification 2001-44/Ultraviolet Protection Test). SPF Analyzer (Optometrics, SPF-290s) was used as an apparatus for measuring the solar protection factor. A thin film-shape tape was used as a test tape, the thin film-shape tape having no absorption peak and high UV permeability. The spherical particle prepared in Example 5 was mixed with the same amounts of 5% and 10% vaseline solutions, respectively, and applied on the tape to be 2.0 mg/cm².

After the tape was placed for 15 minutes at normal temperature, the solar protection factor was estimated using SPF analyzer. The solar protection factor was referred to as a mean of three-times experimental values.

As a result, the mean values obtained in 5% and 10% vaseline solutions were 2.89±0.33 and 5.68±0.35, respectively. These values correspond to about 50% of the solar protection factor of octylmethoxycinnamate used as a liquid UV-protecting agent in a form of molecule. Accordingly, the tape has a very superior performance, considering the size of the particle.

INDUSTRIAL APPLICABILITY

Accordingly, the polysilsesquioxane spherical particle according to the present invention has a simple and economical method of manufacturing the spherical particle, a superior skin safety, and a superior miscibility with the other components of the cosmetics. In particular, the polysilsesquioxane spherical particle according to the present invention has a excellent UV-protecting efficiency when it is used as a cosmetics additive since it contains the UV-absorbing group in both the inside and outside surfaces.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. A method of manufacturing a polysilsesquioxane spherical particle containing a UV absorbing group, the method comprising:
   (i) preparing a silsesquioxane precursor (A) containing the predetermined UV-absorbing group;
   (ii) adding a surfactant to a predetermined solvent; and
   (iii) reacting the silsesquioxane precursor (A) prepared in the step (i) with a compound (B) or its oligomer (B') of a following Chemical Formula 1 under the predetermined solvent by means of a catalyst or a co-polymerization precursor to prepare a polysilsesquioxane spherical particle containing a UV-absorbing group:

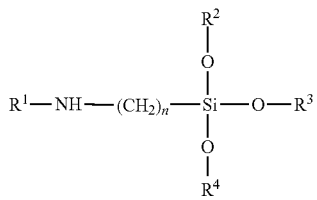

Chemical Formula 1 wherein $R^1$ is selected from the group consisting of hydrogen, an alkyl group, an aminoketyl group, an aryl group, an aminoalkylaminoalkyl group, an aminoalkyl group, an aminocycloalkyl group, an aminoalkenyl group, an aminocycloalkenyl group and an aminoallyl group; n is an integral number of 1 to 3; $R^2$, $R^3$ and $R^4$ are selected from the group consisting of an alkyl group, a cycloalkyl group, an alkenyl group, a cycloalkenyl group and an aryl group and wherein the silsesquioxane precursor (A) is at least one material selected from the group consisting of trimethoxysilylpropylbenzamide, N-trimethoxysilylpropyl-p-methoxycinnamamide and trimethoxysilylpropylcinnamamide.

2. The method of manufacturing the polysilsesquioxane spherical particle containing the UV-absorbing group according to the claim 1, further comprising reacting the compound (B) of the Chemical formula 1 with moisture/water and forming the oligomer (B').

3. The method of manufacturing the polysilsesquioxane spherical particle containing the UV-absorbing group according to any one of the claims 1 and 2, wherein the compound (B) of the Chemical Formula 1 is 3-aminopropyltrimethoxysilane or N-(2-aminoethyl)-3-aminopropyltrimethoxysilane.

4. The method of manufacturing the polysilsesquioxane spherical particle containing the UV-absorbing group according to any one of the claims 1 and 2, wherein the UV-absorbing group included in the silsesquioxane precursor (A) is produced by using at least one material selected from the group consisting of cinnamic acid, methoxycinnamic acid, benzoic acid, N,N-dimethyl-p-aminobenzoic acid, N,N-dihydroxypropyl-p-aminobenzoic acid, and the derivatives thereof.

5. The method of manufacturing the polysilsesquioxane spherical particle containing the UV-absorbing group according to any one of the claims 1 and 2, wherein the predetermined solvent in the step (ii) is selected from the group consisting of water, ethanol containing water, methanol containing water, propanol containing water, isopropanol containing water, tetrahydrofuran containing water, acetone containing water, dioxane containing water, dioxaneethyleneglycolmethylether containing water, ethyleneglycolethylether containing water or propyleneglycolethylether containing water; or a combination of at least two solvents selected from the group.

6. The method of manufacturing the polysilsesquioxane spherical particle containing the UV-absorbing group according to the claim 1, wherein the surfactant is at least one material selected from the group consisting of polyoxyethylene sorbitan, sorbitan fatty acid ester and cetyltriaminobromide.

* * * * *